(12) United States Patent
Pederson

(10) Patent No.: US 9,649,499 B2
(45) Date of Patent: May 16, 2017

(54) METHOD FOR INHIBITING PLATELET INTERACTION WITH BIOMATERIAL SURFACES

(75) Inventor: Brian Pederson, Plymouth, MN (US)

(73) Assignee: Medtronic ATS Medical, Inc., Minneapolis, MN (US)

(*) Notice: Subject to any disclaimer, the term of this patent is extended or adjusted under 35 U.S.C. 154(b) by 2887 days.

(21) Appl. No.: 12/057,729

(22) Filed: Mar. 28, 2008

(65) Prior Publication Data

US 2008/0243198 A1    Oct. 2, 2008

Related U.S. Application Data

(60) Provisional application No. 60/908,576, filed on Mar. 28, 2007.

(51) Int. Cl.
| | | |
|---|---|---|
| *A61N 1/375* | (2006.01) | |
| *A61L 33/00* | (2006.01) | |
| *A61L 33/12* | (2006.01) | |
| *A61N 1/05* | (2006.01) | |

(52) U.S. Cl.
CPC .......... *A61N 1/375* (2013.01); *A61L 33/0094* (2013.01); *A61L 33/126* (2013.01); *A61N 1/05* (2013.01); *Y10T 428/31768* (2015.04)

(58) Field of Classification Search
CPC ..... A61N 1/36; A61N 1/3605; A61N 1/36014
USPC .......................................................... 607/2
See application file for complete search history.

(56) References Cited

U.S. PATENT DOCUMENTS

| | | | |
|---|---|---|---|
| 3,609,768 A | * 10/1971 | Ayres | A61B 5/076 |
| | | | 514/56 |
| 3,757,794 A | 9/1973 | Cannon et al. | |
| 3,914,802 A | * 10/1975 | Reick | 623/1.43 |
| 4,038,702 A | * 8/1977 | Sawyer | A61F 2/0077 |
| | | | 205/680 |
| 4,945,912 A | 8/1990 | Langberg | |
| 4,979,955 A | 12/1990 | Smith | |
| 5,078,763 A | 1/1992 | Blount-Gillette | |
| 5,348,553 A | 9/1994 | Whitney | |
| 5,464,438 A | * 11/1995 | Menaker | 623/1.43 |
| 5,578,073 A | 11/1996 | Haimovich et al. | |
| 5,603,731 A | 2/1997 | Whitney | |
| 5,648,330 A | 7/1997 | Pierschbacher et al. | |
| 5,741,852 A | 4/1998 | Marchant et al. | |
| 5,895,419 A | * 4/1999 | Tweden et al. | 623/2.36 |

(Continued)

FOREIGN PATENT DOCUMENTS

| | | |
|---|---|---|
| EP | 0 643 601 A1 | 1/2001 |
| SE | 1 566 472 | 4/1980 |

(Continued)

OTHER PUBLICATIONS

Qui et al., "Convenient and Effective Method for Removing Fibrinogen from Serum Specimens before Protein Electrophoresis", Clinical Chemistry, 2003, vol. 49, No. 6, pp. 868-872.

(Continued)

*Primary Examiner* — Christopher D Koharski
*Assistant Examiner* — Roland Dinga

(57) ABSTRACT

A method for passivating a biomaterial surface includes modifying proteinaceous material disposed at the biomaterial surface. The passivation may be effectuated by exposing the biomaterial surface to therapeutic electrical energy in the presence of blood or plasma.

14 Claims, 6 Drawing Sheets

(56) References Cited

U.S. PATENT DOCUMENTS

| | | | |
|---|---|---|---|
| 5,924,975 | A | 7/1999 | Goldowsky |
| 5,986,168 | A | 11/1999 | Noishiki |
| 5,993,890 | A | 11/1999 | Marchant et al. |
| 6,013,625 | A | 1/2000 | Pierschbacher et al. |
| 6,047,700 | A | 4/2000 | Eggers et al. |
| 6,110,204 | A | 8/2000 | Lazarov et al. |
| 6,206,914 | B1 | 3/2001 | Soykan et al. |
| 6,632,215 | B1 | 10/2003 | Lemelson |
| 6,658,288 | B1 | 12/2003 | Hayashi |
| 7,071,235 | B2 * | 7/2006 | Guire et al. ............ 514/686 |
| 7,132,408 | B2 | 11/2006 | Boyer et al. |
| 7,166,612 | B2 | 1/2007 | Flaumenhaft |
| 7,745,223 | B2 * | 6/2010 | Schubert et al. ......... 436/69 |
| 2001/0000802 | A1 | 5/2001 | Soykan et al. |
| 2002/0120297 | A1 | 8/2002 | Shadduck |
| 2002/0188323 | A1 * | 12/2002 | Penner et al. ............ 607/2 |
| 2003/0229376 | A1 | 12/2003 | Sandhu |
| 2004/0210282 | A1 | 10/2004 | Flock et al. |
| 2004/0215310 | A1 | 10/2004 | Amirana |
| 2004/0229333 | A1 | 11/2004 | Bowlin |
| 2004/0243225 | A1 | 12/2004 | Ragheb et al. |
| 2005/0021134 | A1 * | 1/2005 | Opie ..................... 623/2.2 |
| 2005/0143802 | A1 | 6/2005 | Soykan et al. |
| 2006/0034734 | A1 * | 2/2006 | Schubert et al. ......... 422/101 |
| 2007/0010702 | A1 | 1/2007 | Wang et al. |

FOREIGN PATENT DOCUMENTS

| | | |
|---|---|---|
| WO | WO 88/01155 | 2/1988 |
| WO | WO 93/25273 | 12/1993 |
| WO | WO 94/11411 | 5/1994 |
| WO | WO 94/25081 | 11/1994 |
| WO | WO 95/19796 | 7/1995 |
| WO | WO 99/36193 | 7/1999 |
| WO | WO 99/44519 | 9/1999 |
| WO | WO 03/037400 | 5/2003 |
| WO | WO 2005/004754 | 1/2005 |

OTHER PUBLICATIONS

Grunkemier et al., "The Effect of Adsorbed Fibrinogen, Fibronectin, von Willebrand Factor and Vitronectin on the Procoagulant State of Adherent Platelets", Biomaterials, 2000, vol. 21, No. 22 (Nov), pp. 2243-2252.

Grunkemeier et al., "Platelet Adhesion and Procoagulant Activity Induced by Contact with Radiofrequency Glow Discharge Polymers: Roles of Adsorbed Fibriogen and vWF", J Biomed Mater Res., 2000, vol. 51 No. 4, pp. 669-679.

Tsai et al., "Variations in the Ability of adsorbed Fibrinogen to Mediate Platelet Adhesion to Polystryene-Based Materials: A Multivariate Statistical Analysis of Antibody Pinding to the Platelet Binding Sites of Fibrinogen", J Biomed Mater Res A, 2003, vol. 67 No. 4, pp. 1255-1268.

Pfister et al., "Late Clinical Events after Clopidogrel Discontinuation may Limit the Benefit of Drug-Eluting Stents: An Observational Study of Drug-eluting Versus Bare-Metal Stents", J Am. Coll Cardiol., 2006, vol. 48 No. 12, pp. 2584-2591.

* cited by examiner

METHOD FOR INHIBITING PLATELET INTERACTION WITH BIOMATERIAL SURFACES

CROSS-REFERENCE TO RELATED APPLICATION

This application claims priority from U.S. provisional application Ser. No. 60/908,576, filed on Mar. 28, 2007 and entitled METHOD FOR INHIBITING PLATELET INTERACTION WITH IMPLANTED MEDICAL DEVICES, the content of which is incorporated herein in its entirety.

FIELD OF THE INVENTION

The present invention relates to providing biomaterial surfaces with thromboresistivity generally, and more particularly to materials and methods for passivating a biomaterial surface so as to inhibit blood platelet interaction therewith.

BACKGROUND OF THE INVENTION

Since the year 2000 alone, more than 1,000,000 vascular prosthetic devices have been implanted worldwide. From stents to artificial heart valves and ventricular assist devices, a wide range of devices are being used to treat patients often expected to live for many years after the procedures. Since biomaterials promote surface-induced thrombotic phenomena to some extent, an ever-increasing pool of patients reliant upon indefinite anticoagulant therapy has been created. This is unfortunate, as the use of drugs like heparin, warfarin and clopidogrel carries a serious risk of side effects like bleeding, bruising and serious internal hemorrhage.

Blood contacting biomaterial surfaces in particular, have been shown to adsorb a layer of proteins from blood and to attract platelets. Build-up of blood components on the surface of implanted devices may reduce their effectiveness, and in many cases will lead to serious adverse complications or operational failure. Thrombogenesis presents a major problem associated with the clinical use of all kinds of prosthetics, and the prevention of unwanted clotting without the side effects incurred through the use of blood thinning drugs would be a major advancement in the field of biomaterials.

One method for securing biomaterials against unwanted thrombosis is to modify the biomaterial surface itself. For example, anti-thrombogenic materials have been covalently bonded onto the blood-contacting biomaterial surfaces. Additionally, the biomaterial has been treated to give its surface a fixed charge which can affect the biocompatibility of the material. In other cases, the surface has been polished to an extremely high degree. Non of these techniques, however, have been completely effective in deterring platelet adhesion to the biomaterial surface.

It has been theorized that promoting adhesion of albumin to the detriment of fibrinogen at the blood-contacting surface could be effective in altering the thrombogenicity of various materials. In fact, Grunkemeier et al., *Biomaterials*, November, 2000 pp. 2243-2252, and Tsai et al., *Journal of Biomedical Materials Research* Dec. 15, 2003, pp. 1255-68, found that the amount of adsorbed fibrinogen was the chief determinant of the degree of platelet adhesion, although platelets were most attracted to a surface when a combination of proteins was residing on the surface, including Von Willebrand factor. No preadsorption of particular blood proteins has yet been shown to prevent clotting entirely. It is very difficult to prevent fibrinogen from adhering to the biomaterial surface, and only a small amount of adhered fibrinogen is necessary to start a chain reaction leading to thrombosis.

Some materials coated with anticoagulant agents such as heparin have had limited success in preventing thrombosis. However, heparin coatings will eventually dissolve over time. Drawbacks to agent-eluting surfaces have also been realized. A study by Pfisterer et al., *Journal of American College of Cardiologists*, Dec. 19, 2006 pp. 2592-5 regarding the Basel Stent Kosten Effektivitats Trial, Late Thrombotic Events, suggested that between 7 and 18 months after implantation, the rates of nonfatal myocardial infarction, death from cardiac causes, and angiographically documented stent thrombosis were higher with drug-eluting stents than with bare metal stents.

Overall, there have been no recognized clinical advancements that could warrant replacing traditional anticoagulation therapy. At this time, only consistent maintenance of a regimen of blood thinning agents is clinically proven to prevent the dangerous thrombotic events associated with implants.

It is a primary object of the present invention to inhibit and/or prevent thrombogenesis and blood platelet adhesion on a biomaterial surface.

It is another object of the present invention to inhibit and/or prevent blood platelet adhesion and thrombogenesis on an electrically conductive, blood-contacting surface of an implantable device.

It is a further object of the present invention to provide an anti-thrombogenic characteristic to biomaterial surfaces by providing certain blood proteins thereat.

It is a further object of the present invention to provide an anti-thrombogenic characteristic to biomaterial surfaces by providing conformationally-modified blood proteins thereat.

It is a still further object of the present invention to provide a method to pre-treat biomaterials such as pyrolytic carbon, titanium, nitinol, and stainless steel using therapeutic electrical energy so as to prevent blood platelet adhesion to the pre-treated biomaterials.

SUMMARY OF THE INVENTION

By means of the present invention, biomaterial surfaces may be provided with a thromboresistant characteristic, such that blood-contacting surfaces of a biomaterial inhibits blood platelet interaction and adhesion therewith. Such passivation of the biomaterial surface is effectuated through a passivating procedure, which may involve application of therapeutic electrical energy and/or deposition of certain proteinaceous materials thereat. Biomaterial surface passivation may be accomplished in vivo, ex-vivo, or in vitro, and may be done prior to, or subsequent to implantation of a biomaterial in a patient.

In one embodiment, a method for passivating a biomaterial surface involves exposing the biomaterial surface to therapeutic electrical energy in the presence of blood or plasma.

Another method for passivating a biomaterial surface includes modifying proteinaceous material disposed thereat.

The biomaterial surface may also be passivated by exposing a quantity of blood or plasma to therapeutic electrical energy and subsequently depositing proteinaceous material from such quantity of blood or plasma on the biomaterial surface.

A biomaterial surface effective in inhibiting blood platelet adhesion thereto includes conformationally modified fibrinogen.

A still further method for passivating a biomaterial surface includes modulating a preferential adsorption of blood proteins to the biomaterial surface.

DETAILED DESCRIPTION OF THE PREFERRED EMBODIMENTS

Figure 1:
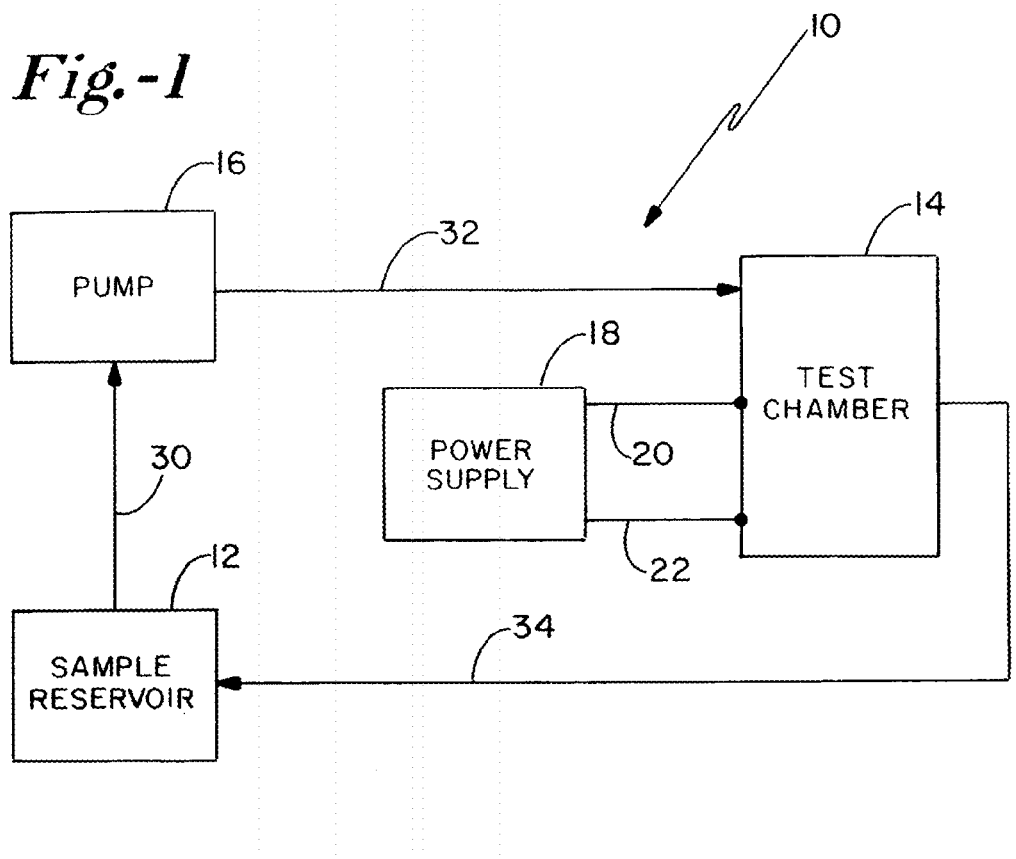
FIG. 1 is a schematic diagram of a testing apparatus used in the testing of the materials and methods of the present invention.

The objects and advantages enumerated above together with other objects, features, and advances represented by the present invention will now be presented in terms of detailed embodiments. Other embodiments and aspects of the invention are recognized as being within the grasp of those having ordinary skill in the art.

The present invention is drawn to techniques and materials which have been found to be useful in inhibiting platelet interaction with biomaterial surfaces. Such interaction may include, for example, adhesion, aggregation, thrombosis, clotting, and/or coagulation of blood platelets at a biomaterial surface exposed to such platelets. For the purposes of this application, the terms "passivate", "passivated", or "passivating" shall refer to a surface that exhibits anti-thrombogenic properties so as to inhibit thrombosis thereat. In some instances, such term may further connote improving the biocompatibility of the surface, such as through thromboresistant properties. For the purposes of this application, "thromboresistant" and "anti-thrombogenic" may be used interchangeably.

A variety of biomaterials may be passivated through the present invention. Most commonly, however, biomaterials include those materials thought to be useful in the fabrication of medical articles, such as implantable medical articles. However, the techniques and materials of the present invention may indeed facilitate the use of "biomaterials" which, in the absence of the techniques and materials of the present invention, would not typically be considered in medical applications, such as in implantable medical articles. Accordingly, as used herein, "biomaterials" is intended to include any native, natural, and/or artificial material used in a biological application, such as in the contacting of blood, plasma, or other biological fluids. Example biomaterials may include metal such as stainless steel, nitinol, and titanium, plastics such as polyolefins, polyesters, polystyrenes, polyurethanes, polyamides, polytetrafluoroethylenes, polysiloxanes, polyimides, phenolics, amino-epoxy resins, polyacrylonitriles, polymethacrylates, silicones, and silicone rubbers, as well as other materials such as pyrolytic carbon and ceramics. In some embodiments of the invention, electrically conductive materials, such as those having an electrical resistivity of less than about 5 ohms may be utilized, though such resistivity threshold may be overcome by using higher voltage potentials. The biomaterials may be used in medical articles including vascular stents, grafts, heart valves, heart diaphragms, catheters, implantable pacemakers, defibrillators, and related leads, sutures, needles, tubing, dialysis membranes, filters, and the like.

The Applicant has focused studies on the thromboresistant properties exhibited by proteinaceous materials contained in or derived from blood. Example such proteinaceous materials that have been addressed in this effort include albumin and fibrinogen. One thromboresistant factor that has been developed in the present studies is a conformationally altered fibrinogen. In its standard form, fibrinogen includes three distinct "conformations", each having slightly different molecular weights. These may be referred to as alpha, beta, or gamma fibrinogen. Such distinct conformations can be viewed through gel electrophoresis, wherein three distinct bands are prevalent at between about 50 kD. Subsequent to exposure to the electrical energy as described herein, the relative concentrations of the fibrinogen conformations at the biomaterial surface are modified. In one embodiment, at least one of the three fibrinogen conformations exposed to the therapeutic electrical energy is found at significantly higher concentrations at a surface exposed to the electrical energy than the concentration of such fibrinogen conformation at a surface not exposed to the therapeutic electrical energy. In addition, at least one fibrinogen conformation concentration is significantly decreased upon electrical stimulation. It is hypothesized that the binding factor of fibrinogen to blood platelets is modified or eliminated through the fibrinogen conformational adjustment described above. As such, the conformationally altered fibrinogen has little or no adhering interaction with blood platelets, thereby effectuating a thromboresistant characteristic.

Another thromboresistant factor of the present invention is the preferential promotion of albumin adhesion to a biomaterial surface. Biomaterials having a relatively high surface concentration of albumin have been shown to inhibit fibrin cascade and platelet attachment, potentially through disruption of electric charge-related platelet interactions. Typically, however, fibrinogen is often the dominant protein adsorbed from protein mixtures such as blood, blood serum, or plasma. Because fibrinogen, in its standard form, is known to promote platelet adhesion at a surface, preferential albumin adsorption acts to inhibit platelet adhesion both through the thromboresistant properties of albumin and through the reduction of fibrinogen presence at the surface.

One technique for effectuating one or more of the thromboresistant factors described above at a biomaterial surface involves the application of electrical energy to proteinaceous material found in blood and/or the application of electrical energy to a biomaterial surface while in the presence of such proteinaceous material. The application of electrical energy, such as a magnitude of electrical energy deemed therapeutic, to blood or plasma has surprisingly been found to cause thromboresistance in biomaterial surfaces contacted with the treated blood or plasma. It is theorized that the thromboresistance generated at the biomaterial surface is derived from one or both of the presence of conformationally altered fibrinogen and the disproportionately high concentration ratio of albumin to standard fibrinogen at such biomaterial surface. Moreover, it is theorized that the existence of such thromboresistant factors at the biomaterial surface is created through the application of therapeutic electrical energy to proteinaceous material contained in blood, blood serum, or plasma, wherein such proteinaceous material includes albumin and/or fibrinogen. Through experimentation, Applicant has determined that application of electrical energy, in the therapeutic magnitudes described herein, establishes an environment for the creation of a thromboresistant, passivated biomaterial surface characteristic. Applicant contemplates, however, that alternative methods may be employed to establish the thromboresistant factors described herein, and to provide a biomaterial surface with one or more of such factors.

In one embodiment, a biomaterial surface may be passivated by exposing such biomaterial surface to therapeutic electrical energy in the presence of blood or plasma. In another embodiment, a biomaterial surface may be passivated by exposing such biomaterial surface to blood or plasma which has been treated with therapeutic electrical energy. In a further embodiment, a biomaterial surface may be passivated by adsorbing at such surface blood proteins treated with therapeutic electrical energy. In another embodiment, a thromboresistant biomaterial surface may be achieved through the provision of a conformationally altered fibrinogen thereat. Other embodiments in addition to those described above are also contemplated as being within the scope of the present invention.

Investigations have been conducted into the prevention of biomaterial surface/platelet interaction with the application of electric current to various materials. Initial studies have focused on the reaction of pyrolytic carbon, stainless steel, nitinol, and titanium. Currently marketed cardiac and vascular stents are primarily made of stainless steel (also carbon coated), and nitinol. In initial experiments, pyrolytic carbon was chosen due to previous experience with this material. The type and magnitude of electrical energy (frequency and current) needed to provide thromboresistance on the surface of carbon have been investigated using an in-vitro blood perfusion system, as described below. Assessment of the reactions has been accomplished through scanning electron microscopy (SEM), electrophoresis, Indium (radioactive) platelet labeling, protein assay assessment, and Fluorochrome-labeled antibody staining.

Test System

A blood perfusion system (BPS) was developed for the evaluation of the biomaterial surfaces and its reaction to blood, and was designed to hold any one of the biomaterials of interest. A schematic diagram of blood perfusion system 10 is illustrated in FIG. 1, and includes a sample reservoir 12, a test chamber 14, and a fluid pump 16 for pumping sample fluid throughout system 10. An electrical power supply 18 is electrically coupled to test chamber 14 through electrical leads 20, 22, and may controllably apply electrical energy to test chamber 14. System 10 further includes fluid conduit sections 30, 32, 34 for transporting the sample fluid throughout system 10.

Sample reservoir 12 of system 10 may be any type of reservoir for the fluids utilized in the test procedure. By way example, such fluids may include whole blood, platelet-rich plasma, or platelet-poor plasma. In some cases, a suspension such as sodium citrate or sodium heparin may be added to the fluid to inhibit spontaneous clotting. Sample reservoir 12 in the test apparatus was a 0.5 liter glass bottle.

Both a pulsatile pump and a roller pump were utilized as pump 16 of system 10. The roller pump, which was a Model 323 pump manufactured by Watson Marlow was utilized in continuous flow regimes at a flow rate of 600 ml per minute. A MOX106 pulsatile pump manufactured by Waters Instruments was calibrated to mimic a beating human heart, wherein a pump surge rate of 70-80 surges per minute was set with an output volume of 50 ml per surge. Pump 16 pumped the sample fluid throughout conduit sections 30, 32, 34, which comprise silicon rubber tubing. In particular, pump 16 pumps the sample fluid from sample reservoir 12 to test chamber 14, and then back to sample reservoir 12.

Figure 2:
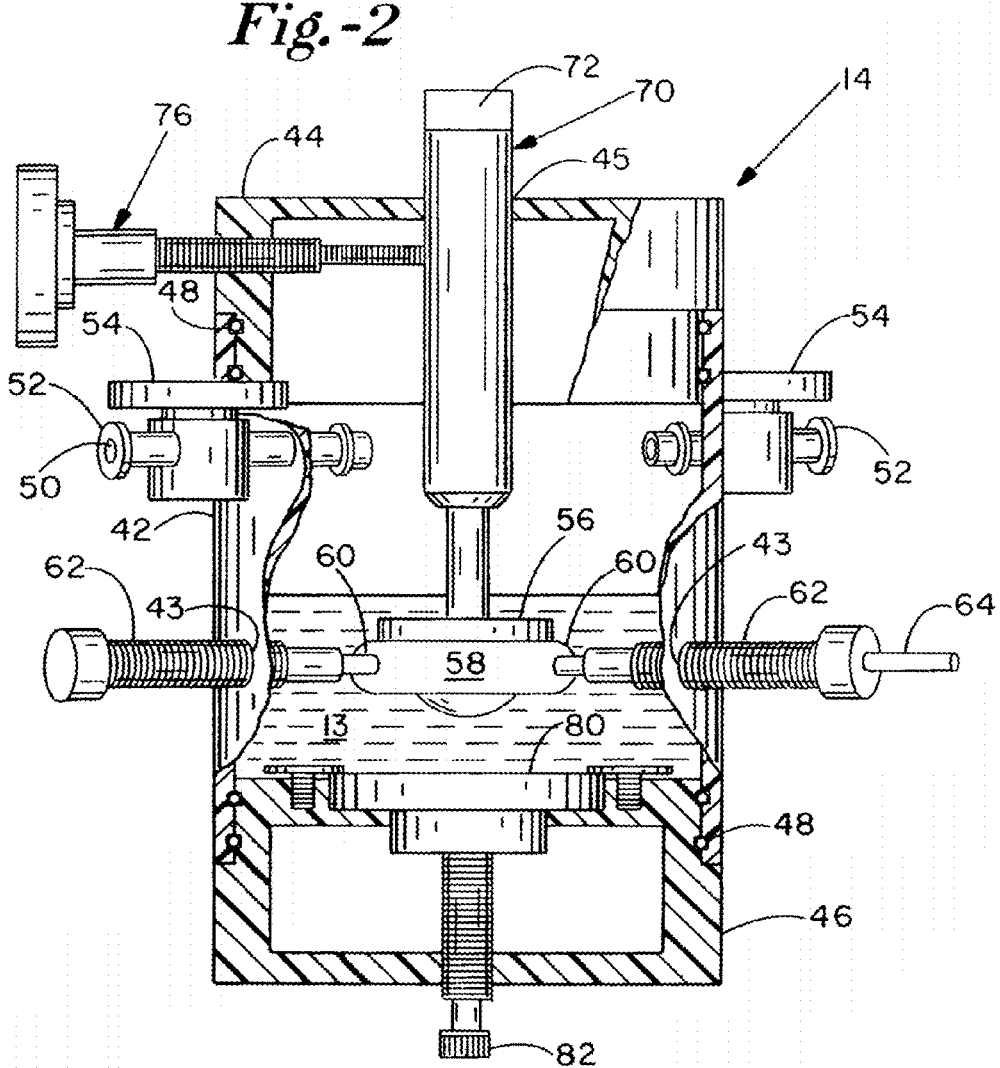
FIG. 2 is a partial cut-away view of a portion of the testing apparatus illustrated in FIG. 1.
Figure 3:
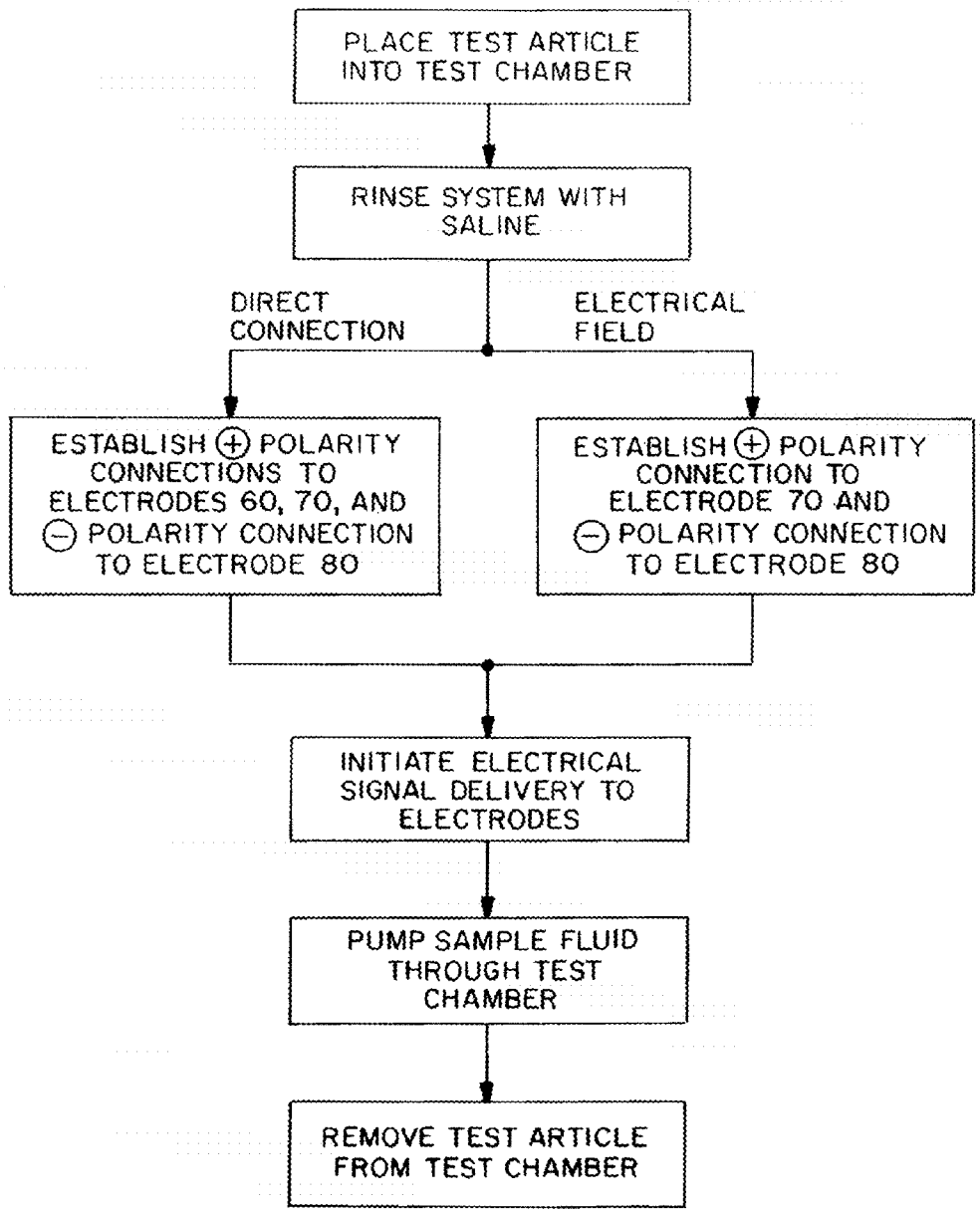
FIG. 3 is a process flow diagram of the testing procedure for testing the methods and materials of the present invention.

Test chamber 14 is illustrated in greater detail in FIG. 2, wherein test chamber 14 includes a polycarbonate housing 42, a top lid 44 and a bottom lid 46. The top and bottom polycarbonate lids 44, 46 are sealingly engageable with housing 42 via O-rings 48. The sample fluid is supplied to test chamber 14 at fluid inlet 50, and is removed from test chamber 14 at fluid outlet 52. Valves 54 were positioned at fluid inlet and fluid outlet 50, 52 for additional control of fluid flow through test chamber 14. The biomaterial surface analyzed in test chamber 14 was a prosthetic bi-leaflet heart valve 56 fabricated from pyrolytic carbon, and further provided with a fabric suture cuff 58 in conventional fashion. The prosthetic heart valve was a 25 mm ATS Open Pivot™ aortic valve having a leaflet surface area of about 12.4 cm².

To suspend the valve prosthesis within test chamber 14, a titanium pin retainer 60 with electrically insulative plastic covers 62 were retained at apertures 43 of housing 42, and pierced the fabric suture cuff 58 of valve prosthesis 56. At least one pin retainer 60 was placed into contact with the pyrolytic carbon body of valve prosthesis 56 so as to make electrical contact to at least the valve body of valve prosthesis 56. In addition, such at least one pin retainer includes an exposed extension portion 64 to which electrical connection may be made. This pin retainer 60 thus forms an electrode for establishing direct electrical contact with valve prosthesis 56. A further electrode 70 is provided through an aperture 45 in top lid 44, with titanium electrode 70 extending into the chamber defined by housing 42 and into contact with the valve leaflets of valve prosthesis 56. In this manner, direct electrical contact to valve prosthesis 56 could be established by connecting an electrical lead to connection end 72 of electrode 70. A set screw 76 was utilized in order to adjust the vertical position of electrode 70 within test chamber 14, and particularly into and out from electrical contact with valve prosthesis 56.

A still further electrode 80 was provided in test chamber 14, wherein titanium electrode 80 is exposed to the sample fluid 13, but is spaced from valve prosthesis 56. Electrical connection to electrode 80 could be made at connection end 82 thereof. As illustrated in FIG. 2, the level of sample fluid 13 was above valve prosthesis 56, such that valve prosthesis 56 was submerged in the sample fluid 13 during the test procedure.

Power supply 18 was a combination of a Tektronix™ AFG310 arbitrary waveform generator which is capable of producing multiple electrical waveforms (sin, triangular, square, and pulsatile) and a custom precision voltage to current converter capable of delivering various current levels. Electrical leads from power supply 18 were connected to respective ones of the electrodes 60, 70, 80 during the test procedure. In some cases, positive polarity was coupled to both electrodes 60 and 70 while negative polarity was coupled to electrode 80. In other cases, positive polarity was coupled only to electrode 70 while negative polarity was coupled to electrode 80. Electrical connection was established at the terminus of the electrical leads through conventional electrical clips.

Test Procedure

The evaluation procedure was as follows:

A test article was inspected and cleaned with alcohol, and then placed in test chamber 14 as described above. A 250 ml reservoir of saline was placed in a water bath at 37° C. Once the saline reached equilibrium temperature, the open ends of conduit sections 30, 34 were placed in the reservoir. Pump 16 was activated and adjusted to a flow rate of 600 ml per minute to pump the saline through system 10 for ten minutes to rinse the system and to test for potential leakage.

In "direct connection" tests, positive polarity electrical connections are made to electrodes 60, 70, and a negative polarity electrical connection is made to electrode 80. Moreover, in "direct connection" tests, electrode 70 is positioned so as to make direct contact with at least a portion of the test biomaterial article. In the case of valve prosthesis 56, electrode 70 may be placed in direct contact with the pyrolytic carbon leaflets when conducting a "direct connection" test.

In "electrical field" tests, positive polarity electrical connection is made to electrode 70 and negative polarity electrical connection is made to electrode 80. Electrode 70 is vertically positioned within test chamber 14 so as to be out of contact with the test article during the application of electrical energy.

Power supply 18 was calibrated to provide a signal having positive going (2.25 V/2.25 mA DC offset, a 4.5 V peak pulse which correlates to a 4.5 mA current. The current is derived by making a differential measurement of the signal across a precision 1 kΩ resistor. A duty cycle of 41.6% was assigned (25 ms ON (+4.5 V) and 60 ms OFF (0 V)).

Pump 16 is then turned off and system 10 drained of the saline. A 250 ml reservoir of sample fluid (human whole blood, animal whole blood, blood serum, platelet rich plasma, platelet poor plasma, etc.) replaces the saline reservoir in the water bath set to 37° C. Pump 16 is again activated to expose system 10 to the sample fluid. Upon completion of the test period, the sample fluid is drained from system 10 and system 10 is then immediately flushed with saline through the process described above.

The test article is then removed from test chamber 14, rinsed in saline, and placed in a solution of gluteraldehyde to arrest further cell action and interaction. The test article is then dehydrated with ethanol to enable assessment of the article surface within the scanning electron microscope vacuum chamber.

EXAMPLES

The invention is further and more specifically illustrated by the following examples and tests.

Example 1

A control experiment was conducted using whole human blood donated within three hours of testing. The whole human blood was pumped through system 10 in the absence of applied electrical energy, and was contacted with a pyrolytic carbon heart valve prostheses at test chamber 14. This test was continued for 30 minutes.

Figure 4:
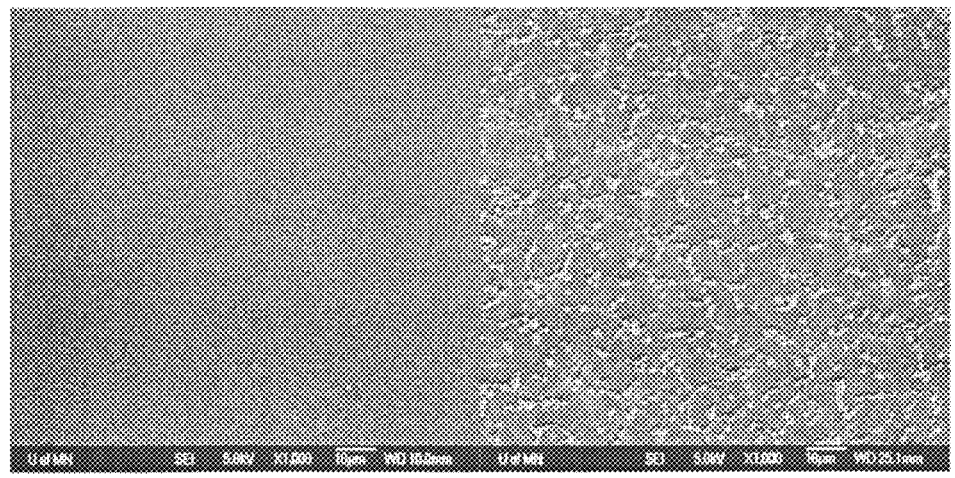
FIG. 4 is a SEM image comparison between a first control test article exposed to whole human blood and a second control test article not exposed to blood.

FIG. 4 illustrates two scanning electron microscope (SEM) slides taken at 1000× magnification. A photograph of a clean, untested pyrolytic carbon valve prosthesis leaflet is shown on the left, and a pyrolytic carbon valve prosthesis leaflet taken from the test article following the control test is shown on the right. It is clear from this control sample that blood platelets are adhered and spread across the surface of the pyrolytic carbon under typical blood exposure conditions, such as those found in vivo. The conditions of the control experiment substantially replicate conditions experienced in vivo for implantable medical articles.

Example 2

Figure 5:
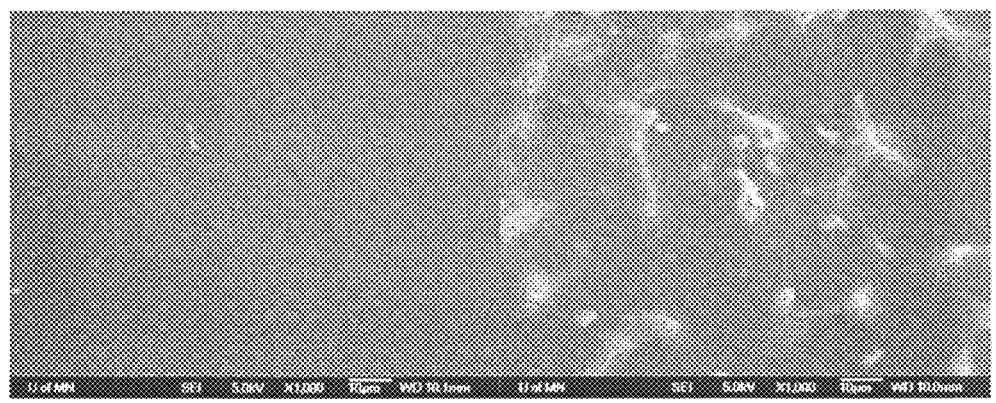
FIG. 5 is a SEM image comparison between a third control test article exposed to whole human blood in an unstimulated environment, with a fourth test article exposed to whole human blood in a stimulated environment.

A sample of whole human blood was separated into two aliquots, with a first aliquot being tested through the "direct connection" procedure described above for 45 minutes. The second aliquot of whole human blood was cycled through system 10 and contacted with a pyrolytic carbon test article in the absence of electrical energy application as a control for 45 minutes. The SEM slides of FIG. 5 demonstrate an image of the control test article surface on the right, and an image of the test article surface used in the "direction connection" test on the left.

It is clear from visual comparison of the SEM slide that the test article surface exposed to the electrical energy is substantially clear of adhered platelets, while the control test article exhibits significant platelet confluency at its surface. A graphical pixilation analysis was performed to derive a quantitation of blood platelet cell presence at the respective test article surfaces. The graphical pixilation analysis was performed by colored pixel count of the SEM images, wherein individual pixel colors other than black were considered adhered platelet cells. The graphical pixilation count analysis of test article surface exposed to electrical energy revealed about 2.5% platelet adhesion, while the control test article surface exhibited about 59.1% platelet cell confluency.

Example 3

A sample of human platelet rich plasma (PRP) was separated into three aliquots with a first aliquot being tested through the "direct connection" procedure described above in a "stagnant" flow regime, wherein the test articles are exposed to a stagnant volume of test fluid for the test period. A first pyrolytic carbon test article was exposed to the first aliquot of PRP in the presence of the electrical energy application described above for 15 minutes. The first pyrolytic carbon test article was then exposed to whole human blood from the PRP donor in a pulsed flow regime for 45 minutes in the absence of applied electrical energy.

A second pyrolytic carbon test article was tested similarly to the first pyrolytic carbon test article, except that the second test article was exposed to PRP in the presence of applied electrical energy for 30 minutes prior to exposure to whole human blood from the PRP donor for 45 minutes in the absence of applied electrical energy.

Control pyrolytic carbon test articles were exposed to PRP in the stagnant chamber for 15 and 30 minutes, respectively, without applied electrical energy, and then exposed to whole human blood from the PRP donor in a pulsed flow regime for 45 minutes in the absence of applied electrical energy.

The test article surfaces were assessed with SEM, and the first and second test articles exhibited significantly less adhered platelets than the amount of adhered platelets observed on the control test article.

Example 4

A sample of human platelet poor plasma (PPP) was separated into three aliquots for testing in connection with three test articles. A first pyrolytic carbon test article was exposed to the first aliquot of PPP in the presence of direct connection electrical energy for 15 minutes. The first pyrolytic carbon test article was then exposed to whole human blood from the PPP donor in a pulsed flow regime for 45 minutes in the absence of applied electrical energy.

A second pyrolytic carbon test article was exposed to PPP in the presence of applied electrical energy for 30 minutes prior to exposure to whole human blood from the PPP donor for 45 minutes in the absence of applied electrical energy.

Control pyrolytic carbon test articles were exposed to PPP in the stagnant chamber for 15 and 30 minutes, respectively, without applied electrical energy, and then exposed to whole human blood from the PPP donor in a pulsed flow regime for 45 minutes in the absence of applied electrical energy.

The test article surfaces were assessed with SEM, and the first and second test articles exhibited significantly less adhered platelets than the amount of adhered platelets observed on the control test article.

Example 5

Bovine blood platelets labeled with indium-111 were used as the sample fluid in a test to determine the ability of passivated test article surfaces to remain effective in the prevention of platelet adhesion over time without continued electrical stimulation. In this "pre-treatment" exercise, four pyrolytic carbon test articles were exposed to the bovine blood for 60 minutes. One of such test articles was electrically stimulated for the entire 60 minute test period. Two test articles were stimulated for 30 minutes during the bovine blood exposure, and then disconnected from the electrical energy for the remaining 30 minutes of the test period. One test article was unstimulated throughout the entire 60 minute test period. The electrical stimulation was conducted at the parameters described above.

Figure 7:
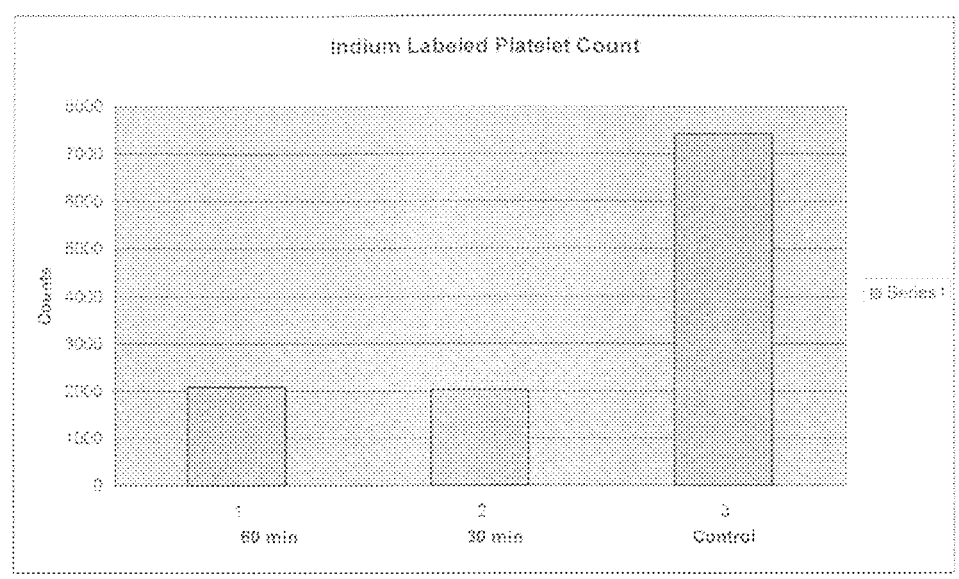
FIG. 7 is a radioactive count chart illustrating platelet concentrations at test articles exposed to different test environments.

The chart of FIG. 7 illustrates radioactive counts for each of the three test groups described above, wherein the radioactive counts are indicative of platelet concentration at the respective test article surface. As demonstrated therein, it appears that pre-treatment of the test article with stimulation in the presence of blood is also effective in inhibiting platelet adhesion even in the absence of continued electrical stimulation. Specifically, the "Group 2" test article surfaces, which were electrically stimulated only for the first 30 minutes of the 60 minute test period, exhibited post-test platelet concentrations similar to the post-test platelet concentrations at the test article surfaces of "Group 1", which received electrical stimulation throughout the 60 minute test period. By contrast, the "Group 3" test article surfaces, which were exposed to blood in the absence of electrical stimulation, exhibited post-test platelet concentrations several fold higher than the platelet concentrations exhibited by either of the stimulated group test articles.

Analysis

A gel electrophoresis analysis was performed on the test article surfaces regarding the blood proteins present thereat. Gel electrophoresis was performed through the use of the microplates procedure of a BCA™ protein assay kit available from Pierce, a division of Thermo Fisher Scientific, Inc., of Rockford, Ill. Proteins taken from 6 test articles, 3 of which were tested in a "stimulated" environment, and the remaining 3 were tested in an "unstimulated" environment by being exposed to blood in the absence of applied electrical energy.

Figure 6:
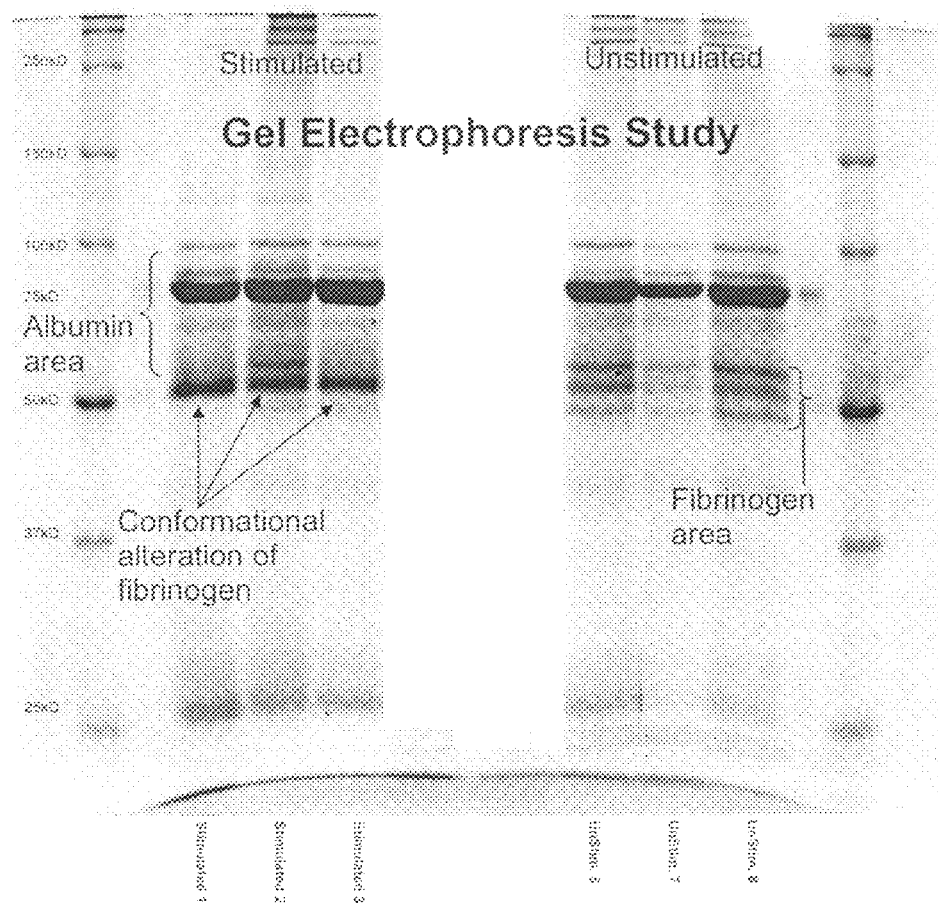
FIG. 6 is a series of gel electrophoresis images comparing surfaces of test articles in a stimulated environment with test articles in an unstimulated environment.

FIG. 6 illustrates results for "stimulated" samples (those tested with exposure to therapeutic electrical energy) versus unstimulated samples (control). The dark bands between 65 and 75 kD indicate the presence of albumin. It appears that the presence of albumin is enhanced by 5-10× in the stimulated group, based on the results of the protein assay. It is well understood that albumin stabilizes charges on materials thereby preventing electric charge-related platelet interactions. The presence of albumin at the surface therefore plays a role in inhibiting platelet interaction/adhesion with the test article surface. It is a surprising result of the above-described tests, however, that application of the utilized levels of electrical energy modulates the preferential adsorption of at least albumin to the test article surface, in that albumin adsorption appears to be significantly preferentially promoted. Such preferential promotion of albumin adsorption is demonstrated by the enhanced albumin presence in the gel electrophoresis slides illustrated in FIG. 6, as well as in the protein assay analyses. It is theorized that the preferential promotion of at least albumin adsorption on the stimulated article surface is caused by the electrical charge provided at the surface through the applied electrical energy.

FIG. 6 further illustrates a conformational alteration of fibrinogen in the stimulated group, as compared to the fibrinogen found on the unstimulated test article surfaces. As described above, the three bands around 50 kD represent alpha, beta, and gamma fibrinogen. The unstimulated article surfaces exhibit all three fibrinogen conformations with approximately similar intensity response through gel electrophoresis. The stimulated test article surfaces, however, exhibited a significantly higher concentration of beta fibrinogen, and a lower concentration of at least alpha fibrinogen and possibly a lower concentration of gamma fibrinogen as well. Of the three fibrinogen conformations, alpha fibrinogen is the lowest molecular weight, and gamma fibrinogen is the highest molecular weight. The concentration changes illustrated by the gel electrophoresis intensity changes in FIG. 6 likely reflects a conformational alteration of the fibrinogen that is related to or induced by electrical stimulation.

The protein assay described above further confirms a substantial increase in fibrinogen concentration at the stimulated test article surfaces, as compared to the fibrinogen concentrations found on the unstimulated test article surfaces. The fibrinogen detected at the surfaces at the stimulated group, however, was conformationally altered as described above. It was determined that the fibrinogen concentration of the stimulated group was 5-10× greater than the fibrinogen concentration of the unstimulated group, thus evidencing a preferential promotion of at least conformationally altered fibrinogen adsorption on the stimulated article surface.

It is theorized that the alteration of fibrinogen receptors caused by the exposure to the therapeutic electrical energy inhibits the binding of further fibrinogen to the surface. The alpha chain of fibrinogen contains the RGDS sequence necessary for platelet interactions. The gamma chain of fibrinogen holds the dodecapeptide sequence (including the RGDS) that can be used for platelet aggregation. Reducing or eliminating the presence of alpha and/or gamma fibrinogen, as seen in the gel electrophoresis images of the stimulated group, may therefore correspondingly inhibit platelet adhesion and aggregation.

Commentary

In view of the above examples and analysis, Applicant has determined that, in one embodiment, therapeutic electrical energy applied to a biomaterial surface, while such surface is exposed to a blood protein-containing fluid such as whole blood or plasma, can passify such biomaterial surface, at least against thrombosis. These studies have further shown that biomaterial surface passivation may be accomplished in a "pre-treatment" arrangement, wherein the biomaterial surface undergoes a passivating procedure and is subsequently placed into a blood platelet-contacting environment. The passivated biomaterial surface exhibits ongoing thromboresistant properties even in the absence of continuing surface passivation. In effect, therefore, a biomaterial surface may be passivated in advance of implantation, with the passivated biomaterial surface remaining effective, at least in the case of thromboresistance, for a significant length of time subsequent to implantation. Accordingly, the methods and materials of the present invention may be utilized, for example, to prevent thrombosis formation in devices such as vascular stents by pre-treating blood-contacting surfaces thereof in the presence of a relatively small amount of the respective patient's blood or plasma prior to device implantation into the patient.

The electrical stimulation described above with reference to the examples, is merely representative of various electrical energy magnitudes that may be useful in passivating biomaterial surfaces. For example, the applied electrical current in the above examples of electropositive 4.5 mA directed to a pyrolytic carbon material having a surface area of about 12.4 cm$^2$ provides a current density of about 0.35 mA/cm$^2$. As described in our co-pending patent application Ser. No. 11/402,463 entitled "System for Conditioning Surfaces in Vivo", the content of which being incorporated herein by reference, an electropositive current density of between about 0.001 and about 1.0 mA/cm$^2$ may also be useful in the present application. Applicant believes that a current density of at least about 0.1 mA/cm$^2$ may be most beneficial for the purposes described herein, depending upon the electrical conductivities of the biomaterials at issue. An upper threshold on the electropositive current density provided at the biomaterial surface for therapeutic conditioning thereof in the present application may be limited only by the current density threshold above which undesired and/or permanent damage to such biomaterial or interfacing material may occur.

For the purposes of this application, therefore, the term "therapeutic electrical energy" shall mean electrical energy that is effective in generating an electropositive current density at the subject biomaterial surface at a magnitude sufficient to passivate the biomaterial surface through exposure of the biomaterial surface to the electrical energy in the presence of blood or plasma. In one embodiment, such therapeutic electrical energy results in an electropositive current density at the biomaterial surface being treated of at least about 0.1 mA/cm$^2$.

As also described above, a further aspect of the present invention is the surprising finding that the deposition of certain blood proteins and/or blood protein concentrations at a biomaterial surface is effective in passivating such biomaterial surface. One passivating material of the present invention is a conformationally altered fibrinogen, and specifically a fibrinogen with a relatively high concentration of beta fibrinogen and/or relatively low concentrations of alpha fibrinogen and/or gamma fibrinogen. Applicant has determined that the presence of such modified fibrinogen at the biomaterial surface at a concentration of at least about 5-10× the concentration of unmodified fibrinogen at an unstimulated surface exposed to blood or plasma for at least about 15 minutes may be effective in passivating the biomaterial surface. As such, Applicant envisions a variety of techniques for depositing a passivating agent, such as conformationally modified fibrinogen, at the biomaterial surface for passivating such biomaterial surface. For example, such a passivating agent may be isolated and used as needed, such as by depositing the passivating agent at a biomaterial surface prior to biomaterial implantation into a patient. Such treatment of the blood-contacting surface of the biomaterial may be performed immediately prior to implantation or significantly prior to implantation, with the passivating agent retaining its passivating properties for a significant period of time subsequent to implantation.

An overall impact, therefore, of the present invention is the prevention of platelet adhesion and thrombogenesis on biomaterial surfaces, including artificial implants, transplants, and native tissue, through the provision of certain modified and/or unmodified blood proteins at such surfaces. In one embodiment, such blood proteins may be provided at the biomaterial surfaces through the application of therapeutic electrical energy to the surface while the surface is in the presence of blood or plasma. Other techniques, however, for the provision of effective passivating agents on target surfaces are envisioned in the present invention.

The invention has been described herein in considerable detail in order to comply with the patent statutes, and to provide those skilled in the art with the information needed to apply the novel principles and to construct and use embodiments of the invention as required. However, it is to be understood that various modifications to the invention can be accomplished without departing from the scope of the invention itself.

What is claimed is:

1. A method for passivating a biomaterial surface, said method comprising:
    exposing said biomaterial surface to therapeutic electrical energy in the presence of blood or plasma prior to implantation within a human body of an object on which said biomaterial surface is located; and
    causing proteinaceous material in the blood or plasma to adhere to said biomaterial surface.

2. A method as in claim 1 wherein said biomaterial surface is a portion of a medical article.

3. A passivated biomaterial surface as in claim 1 wherein said biomaterial surface has an electrical resistivity of less than about 5 ohms.

4. A passivated biomaterial surface as in claim 3 wherein said biomaterial surface is selected from pyrolytic carbon, titanium, nitinol, stainless steel, platinum, or iridium.

5. A method as in claim 1 wherein said therapeutic electrical energy exposure is effected through direct electrical contact between an electrical energy source and said biomaterial surface.

6. A method for passivating a biomaterial surface, said method comprising depositing modified proteinaceous material at said biomaterial surface prior to implantation with a human body of an object on which said biomaterial surface is located.

7. A method as in claim 6 wherein said modified proteinaceous material includes conformationally altered fibrinogen.

8. A method for passivating a biomaterial surface, said method comprising:
    (a) exposing a quantity of blood or plasma to therapeutic electrical energy;
    (b) subsequent to step (a), depositing proteinaceous material from said quantity of blood or plasma on said biomaterial surface;
    (c) subsequent to step (b), implanting in a human body an object on which said biomaterial surface is located; and (d) subsequent to step (c), inhibiting aggregation of blood platelets at said biomaterial surface by the deposited proteinaceous material.

9. A method as in claim 8 wherein said therapeutic electrical energy is effective in conformationally altering fibrinogen contained in said quantity of blood or plasma.

10. A method for inhibiting aggregation of blood platelets at a biomaterial surface, said method comprising:
exposing said biomaterial surface to therapeutic electrical energy in the presence of blood or plasma prior to implantation within a human body of an object on which said biomaterial surface is located; and
causing proteinaceous material in the blood or plasma to adhere to said biomaterial surface to thereby inhibit aggregation of blood platelets at said biomaterial surface.

11. A method as in claim 10 wherein said biomaterial has an electrical resistivity of less than about 5 ohms.

12. A method as in claim 11 wherein said object is selected from the group consisting of pyrolytic carbon, titanium, nitinol, stainless steel, platinum, and iridium.

13. A method as in claim 10 wherein said proteinaceous material includes albumin and fibrinogen.

14. A method for passivating a biomaterial surface, said method comprising modulating the preferential adsorption of blood proteins to said biomaterial surface by exposing said blood proteins to therapeutic electrical energy prior implantation within a human body of an object on which said biomaterial surface is located.

\* \* \* \* \*